United States Patent
Liu

(10) Patent No.: US 6,872,530 B2
(45) Date of Patent: Mar. 29, 2005

(54) METHOD FOR DETERMINING THE PRESENCE OF DNA VARIANTS USING PEPTIDE NUCLEIC ACID PROBES

(75) Inventor: Zhaowei Liu, State College, PA (US)

(73) Assignee: SpectruMedix, LLC, State College, PA (US)

( * ) Notice: Subject to any disclaimer, the term of this patent is extended or adjusted under 35 U.S.C. 154(b) by 0 days.

(21) Appl. No.: 10/128,334

(22) Filed: Apr. 24, 2002

(65) Prior Publication Data

US 2003/0203364 A1 Oct. 30, 2003

(51) Int. Cl.[7] .......................... C12Q 1/68; C12P 19/34; C07H 21/04
(52) U.S. Cl. ........................ 435/6; 435/91.1; 435/91.2; 204/450; 204/456; 204/461; 536/23.1; 536/24.3; 536/24.33
(58) Field of Search ......................... 435/6, 91.1, 91.2, 435/7.1, 287.1; 204/450, 456, 461, 621, 606, 616; 536/23.1, 24.3, 24.33, 22.1, 528, 536; 436/518, 527, 528, 536, 516

(56) References Cited

U.S. PATENT DOCUMENTS

| | | | |
|---|---|---|---|
| 5,066,377 A | | 11/1991 | Rosenbaum et al. |
| 5,068,176 A | | 11/1991 | Vijg et al. |
| 5,736,025 A | * | 4/1998 | Smith et al. .............. 204/621 |
| 5,795,720 A | | 8/1998 | Henco et al. |
| 5,871,908 A | | 2/1999 | Henco et al. |
| 5,998,147 A | | 12/1999 | Petit et al. |
| 6,036,831 A | | 3/2000 | Bishop |
| 6,265,171 B1 | * | 7/2001 | Herman et al. ............ 435/6 |
| 6,265,557 B1 | | 7/2001 | Diamond et al. |
| 6,398,933 B1 | | 6/2002 | Scott |
| 6,475,721 B2 | * | 11/2002 | Kleiber et al. ............ 435/6 |
| 6,486,309 B1 | | 11/2002 | Gerber et al. |
| 6,613,508 B1 | | 9/2003 | Ness et al. |
| 2002/0012902 A1 | * | 1/2002 | Fuchs et al. ............... 435/4 |

FOREIGN PATENT DOCUMENTS

| | | | |
|---|---|---|---|
| WO | WO 91/02815 | 3/1991 | |
| WO | WO 96/08715 | 3/1996 | |
| WO | WO 96/24687 | 8/1996 | |
| WO | WO 01/077386 | 10/2001 | |
| WO | WO 02/31199 A1 | 4/2002 | |
| WO | WO 02/31199 * | 4/2002 | ........... C12P/19/34 |
| WO | WO 02/031199 | 4/2002 | |

OTHER PUBLICATIONS

Ray et al. "Peptide nucleic acid (PNA): its medical and biotechnical applications and promise for the future" Jun. 2000, vol. 14 pp. 1041–1060.*

Wartell et al. (J of Chromatography (1998) 806: 169–185).*

Igloi et al. Biotechniques (1999) 27: 798–808.*

Abrams, Ezra S. et al., "Comprehensive Detection of Single Base Changes in Human Genomic DNA Using Denaturing Gradient Gel Electrophoresis and a GC Clamp," Genomics, 1990, vol. 7, pp. 463–475.

Alper, Joseph, "Biotechnology: Weighing DNA for Fast Genetic Diagnosis," Science Magazine, vol. 279, No. 5359, Mar. 27, 1998, pp. 2044–2045 (pp. 1–3).

(Continued)

Primary Examiner—Carla J. Myers
Assistant Examiner—Alexander H. Spiegler
(74) Attorney, Agent, or Firm—Fish & Richardson P.C.

(57) ABSTRACT

The present invention relates to a peptide nucleic acid probe-based method for generating data indicative of the presence of a nucleotide polymorphism, mutation, or methylated cytosine in a nucleotide containing compound. A peptide nucleic acid probe (PNAP) is subjected to temperature gradient electrophoresis in the presence of a nucleotide containing compound. The PNAP is irradiated to generate a spectroscopic signal. The spectroscopic signal is converted into data suitable for determining the presence of the nucleotide polymorphism or the mutation in the nucleotide-containing compound.

22 Claims, 10 Drawing Sheets

OTHER PUBLICATIONS

Chee, Mark, et al., "Accessing Genetic Information with High–Density DNA Arrays," Science Magazine, vol. 274, No., 5287, Oct. 1996, pp. 610–614 (pp. 1–13).

Gelfi, Cecilia, et al., "Detection of point mutations by capillary electrophoresis in liquid polymers in temporal thermal gradients," Electrophoresis, 1994, vol. 15, pp. 1506–1511.

Henco, K., et al., "Quantitative PCR: the determination of template copy numbers by temperature gradient gel electrophoresis (TGGE)," Nucleic Acids Research, vol. 18, No. 22, pp. 6733–6734.

Ke, Song–hua et al., "Selecting DNA fragments for mutation detection by temperature gradient gel electrophoresis: Application to the p53 gene cDNA," Electrophoresis, 1993, vol. 14, pp. 561–565.

Khrapko, K. et al., "Constant denaturant capillary electrophoresis (CDCE): a high resolution approach to mutational analysis," Nucleic Acids Research, 1994, vol. 22, No. 3, pp. 364–369.

Myers, Richard M. et al., "Detection of single base substitutions in total genomic DNA," Nature, Feb. 1985, vol. 313, pp. 495–498.

Paper entitled, "High–Throughput Detection of Unknown Mutations By Using Multiplexed Capillary Electrophoresis With Polyvinylpyrrolidone Solution," 28 pages.

Riesner, Detlev, et al., "Temperature–gradient gel electrophoresis for the detection of polymorphic DNA and for quantitative polymerase chain reaction," Electrophoresis, 1992, vol. 13, pp. 632–636.

Riesner, Detlev et al., "Temperature–gradient gel electrophoresis of nucleic acids: Analysis of conformational transitions, sequence variations, and protein–nucleic acid interactions," Electrophoresis, 1989, vol. 10, pp. 377–389.

Schell, Jens, et al., "Detection of point mutations by capillary electrophoresis with temporal temperature gradients," Electrophoresis, 1999, vol. 20, pp. 2864–2869.

Sidransky, David, "Nucleic Acid–Based Methods for the Detection of Cancer," Science, vol. 278, Nov. 7, 1997, www.sciencemag.org, pp. 1054–1058.

Taylor, Paul, et al., "Detection of Mutations and Polymorphisms on the WAVE™ DNA Fragment Analysis System," TRANSGENOMIC, Application Note 101.

Wang, David G., "Large–Scale Inditification, Mapping, and Genotyping of Single–Nucleotide Polymorphisms in the Human Genome," Science, vol. 280, May 15, 1998, pp. 1077–1082.

Arghya Ray et al., "Peptide nucleic acid (PNA): its medical and biotechnical applications and promise for the furture", Department of Physical Chemistry, Chalmers University of Technology, S 412 96, Gothenburg, Sweden, pp. 1041–1060.

* cited by examiner

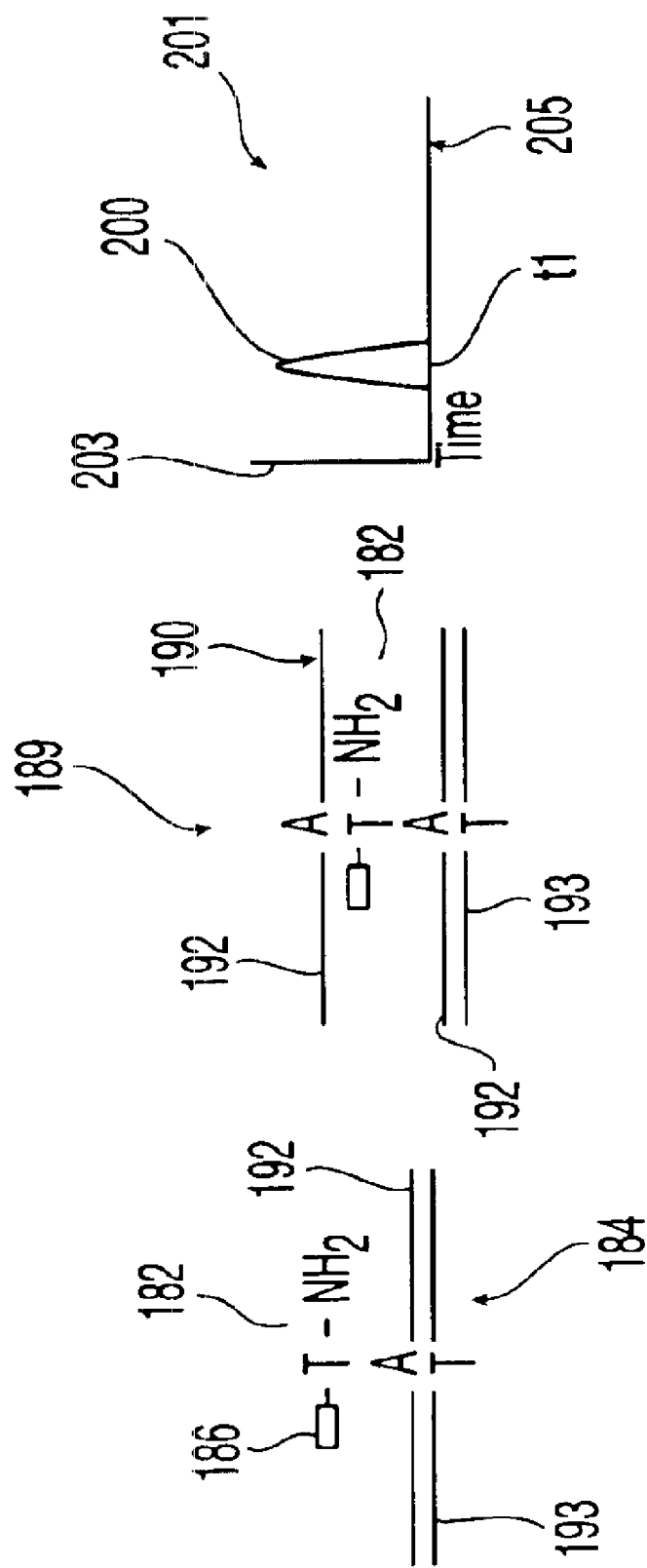

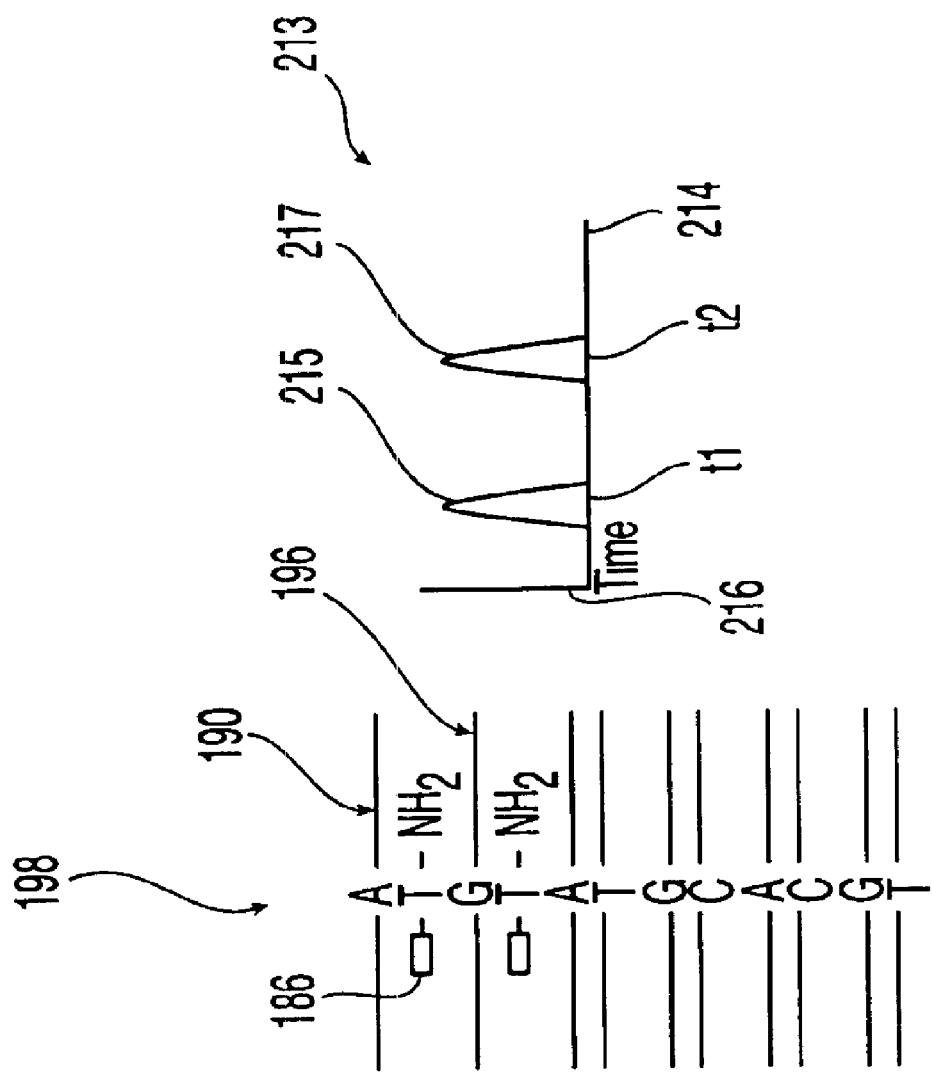

SEQUENCE LISTING

```
<160> NUMBER OF SEQ ID NOS: 10

<210> SEQ ID NO 1
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: n at Position 8 = Methylated cytosine
<220> FEATURE:
<221> NAME/KEY: misc_feature
<222> LOCATION: (1)...(11)
<223> OTHER INFORMATION: Synthesized

<400> SEQUENCE: 1
tactaaanga t                                                         11

<210> SEQ ID NO 2
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 2
atgatttgct a                                                         11

<210> SEQ ID NO 3
<211> LENGTH: 11
```

```
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: n at Position 3 = Uracil
<220> FEATURE:
<221> NAME/KEY: misc_feature
<222> LOCATION: (1)...(11)
<223> OTHER INFORMATION: n at Position 8 = Methylated cytosine
<220> FEATURE:
<221> NAME/KEY: misc_feature
<222> LOCATION: (1)...(11)
<223> OTHER INFORMATION: Synthesized

<400> SEQUENCE: 3
tantaaanga t                                                    11

<210> SEQ ID NO 4
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: n at Position 9 = Uracil
<220> FEATURE:
<221> NAME/KEY: misc_feature
<222> LOCATION: (1)...(11)
<223> OTHER INFORMATION: Synthesized

<400> SEQUENCE: 4
atgatttgnt a                                                    11

<210> SEQ ID NO 5
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 5
tattaaacga t                                                    11

<210> SEQ ID NO 6
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 6
ataatttgct a                                                    11

<210> SEQ ID NO 7
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 7
tactaaacga t                                                    11
```

-continued

```
<210> SEQ ID NO 8
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: n at Position 3 = Uracil
<220> FEATURE:
<221> NAME/KEY: misc_feature
<222> LOCATION: (1)...(11)
<223> OTHER INFORMATION: n at Position 8 = Uracil
<220> FEATURE:
<221> NAME/KEY: misc_feature
<222> LOCATION: (1)...(11)
<223> OTHER INFORMATION: Synthesized

<400> SEQUENCE: 8
tantaaanga t                                                          11

<210> SEQ ID NO 9
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 9
ataatttact a                                                          11

<210> SEQ ID NO 10
<211> LENGTH: 11
<212> TYPE: DNA
<213> ORGANISM: Artificial Sequence
<220> FEATURE:
<221> NAME/KEY: misc_feature
<222> LOCATION: (1)...(11)
<223> OTHER INFORMATION: Synthesized

<400> SEQUENCE: 10
tattaaatga t                                                          11
```

METHOD FOR DETERMINING THE PRESENCE OF DNA VARIANTS USING PEPTIDE NUCLEIC ACID PROBES

FIELD OF THE INVENTION

The present invention relates to a method for determining the presence of variants in nucleotide containing compounds, such as DNA. In particular, a nucleotide containing compound is subjected to temperature gradient electrophoresis in the presence of a probe, such as a peptide nucleic acid probe.

BACKGROUND

There is an increasing demand for genotyping technology to more efficiently detect DNA variations. For example, efficient, fast and cost-effective techniques are still required for analyses of single nucleotide polymorphisms (SNPs) and known mutations associated with disease. Many methods have been developed for SNP/mutation genotyping. DNA-chip methods based on hybridization have the capability of processing large number of samples, but require careful calibration of the signal when interpreting data. Variants can be detected using single base extension (SBE) followed by separation with capillary electrophoresis using an automated sequencing instrument. However, the length of the extension primer that can be synthesized by the present technology limits the number of samples that can be analyzed in a single capillary. For instance, about 6 SBE products or less are separated in a single capillary using the Applied Biosystems' SNaPshot kit (from Protocol of ABI Prism SNaPshot Multiplex Kit, 2000). Detection of SBE reactions by mass spectrometry requires highly purified products, which can be costly and labor-intensive.

SUMMARY OF THE INVENTION

One embodiment of the present invention relates to a peptide nucleic acid probe-based method for generating data indicative of the presence of a variant in a nucleotide containing compound (NCC). The method comprises subjecting an NCC and a peptide nucleic acid (PNA) probe to temperature gradient (TG) electrophoresis.

During at least a portion of the temperature gradient electrophoresis, the NCC and PNA probe are associated, preferably in the form of a complex. The temperature is preferably changed by an amount sufficient to modify, such as to reduce or increase, the association of the PNA probe-NCC complex to thereby change the mobility of the complex.

For example, in a preferred embodiment, the temperature is increased by an amount sufficient to at least partially thermally denature the complex, thereby reducing the association between the PNA probe and NCC. In this embodiment, the PNA probe-NCC complex are preferably introduced to the separation lane, such as a column or capillary in bound form. Thus, when the temperature is increased, the complex at least partially denatures thereby reducing its mobility relative to the fully annealed complex.

In another embodiment, the temperature is decreased by an amount sufficient to at least partially thermally anneal a dissociated complex, thereby increasing the association therebetween. Annealing a partially dissociated complex increases the mobility of the migrating complex.

The NCC and PNA probe are irradiated to generate a spectroscopic signal, which preferably arises from a spectroscopic tag associated with the PNA probe. A preferred spectroscopic signal is fluorescence arising from a fluorescent tag that is bound, preferably covalently, to the PNA probe.

The spectroscopic signal is converted into data, which may be represented as, for example, an electropherogram. The data are suitable for determining the presence of a variant. If a variant is present, the data are preferably indicative of the location of the variant within the NCC. The data may be compared with data derived from temperature gradient electrophoresis of a reference nucleotide containing compound having a known variant status to determine whether or not the NCC includes a variant and, if so, its location.

Examples of variants whose presence can be determined using the present method include single nucleotide polymorphisms and mutations. Examples of variants include base-substitutions or methylated cytosines. An NCC to be tested for presence of variants may include zero, one, or more than one variants.

Preferred NCC's include DNA, such as single or double stranded DNA, and RNA. The NCC may be a product resulting from an amplification process, such as a polymerase chain reaction (PCR). The invention, however, does not require that the NCC be obtained directly or even indirectly from an amplification process, such as PCR.

A preferred PNA probe includes fewer than about 25 nucleotide bases, perhaps fewer than about 20 nucleotide bases, such as fewer than about 15 nucleotide bases. The PNA probe may be significantly shorter than the NCC to which the probe is associated. In one embodiment, at least some of the NCC-PNA probe complexes include an NCC which is, for example, at least about 3, preferably at least about 5, and more preferably at least about 10 times as long as the PNA probe to which it is associated. For example, the NCC may have 3 times, preferably at least about 5, and preferably at least about 10 times as many bases as the PNA probe. Increasing the length difference increases the change in migration rate and, therefore, increases the number of samples that can be separated in a single lane.

Another embodiment of the invention relates to a peptide nucleic acid probe-based method for determining the presence of variants in a plurality of respective nucleotide containing compounds each of which may contain zero, one, or more than one variants.

The method includes subjecting a mixture to temperature gradient electrophoresis. The mixture comprises a plurality of different peptide nucleic acid probes and a plurality of different nucleotide containing compounds. The different peptide nucleic acid probes preferably have different lengths. The different nucleotide containing compounds preferably have different lengths. For example, it is preferred that the lengths of different PNAP's differ from one another by at least about 2 and more preferably at least about 5 base pairs.

The peptide nucleic acid probes are irradiated to generate spectroscopic signals, which are converted to data suitable for determining the presence of variants such as single nucleotide polymorphisms, methylations, or mutations in respective nucleotide-containing compounds.

Yet another embodiment of the invention relates to a peptide nucleic acid probe-based method for determining the presence of a variant in a nucleotide containing compound. The method includes obtaining a first parameter representative of a first spectroscopic signal resulting from a first peptide nucleic acid probe (PNAP). The first spectroscopic signal was preferably obtained upon subjecting the first PNAP to temperature gradient electrophoresis in the presence of the nucleotide containing compound. The method also includes obtaining a second parameter representative of a second spectroscopic signal resulting from a second PNAP. The second PNAP was preferably subjected to temperature gradient electrophoresis in the presence of the nucleotide containing compound. The first and second parameters are compared to determine the presence of a single nucleotide polymorphism or a mutation in the nucleotide-containing compound. Preferred parameters include a migration time, an intensity, a wavelength of fluorescence, a wavelength of absorbance, or combination thereof.

BRIEF DESCRIPTION OF THE DRAWINGS

The present invention is discussed below in reference to the drawings in which:

FIG. 3a shows a probe and a nucleotide containing compound according to the method of FIG. 1;

FIG. 3b shows a mixture formed upon melting and annealing the probe and nucleotide containing compound of FIG. 3a;

FIG. 3c shows an electropherogram obtained upon temperature gradient electrophoresis and irradiation of the mixture of FIG. 3b;

FIG. 4b shows a mixture formed upon melting and annealing the probe and nucleotide containing compound of FIG. 4a;

FIG. 5a shows a probe and a nucleotide containing compounds according to the method of FIG. 1;

FIG. 5b shows a mixture formed upon melting and annealing the probe and nucleotide containing compounds of FIG. 5a;

FIG. 5c shows an electropherogram obtained upon temperature gradient electrophoresis and irradiation of the mixture of FIG. 5b;

FIG. 7b shows a mixture formed upon melting and annealing the probes and nucleotide containing compound of FIG. 7a;

FIG. 8b shows a mixture formed upon melting and annealing the probes and nucleotide containing compound of FIG. 8a;

DETAILED DESCRIPTION OF THE INVENTION

Figure 1:
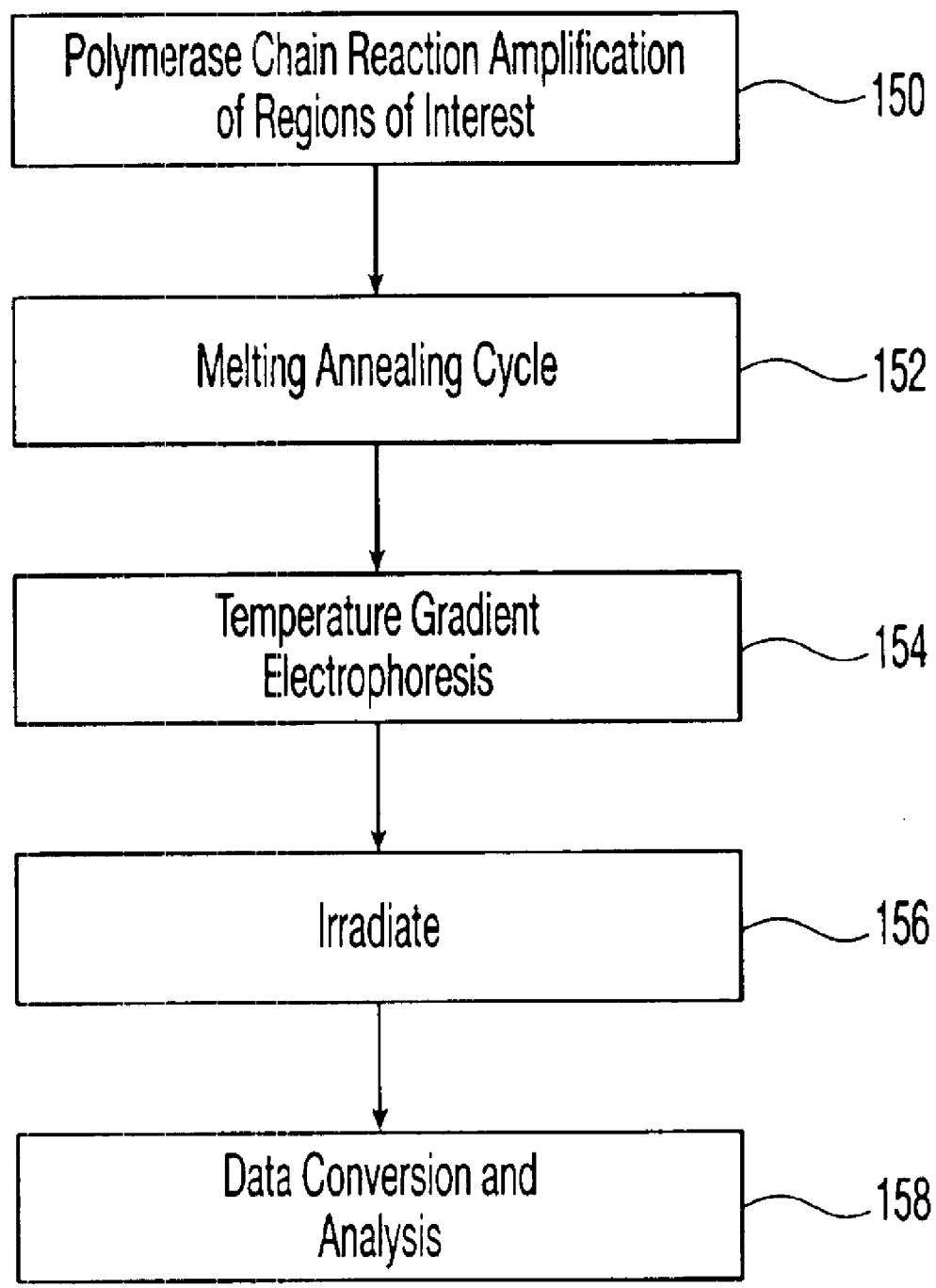
FIG. 1 shows a flow chart showing mutation detection method of the invention.

Referring to FIG. 1, the present invention relates to a method for determining the presence of variants, such as mutations, single nucleotide polymorphisms (SNP's), and methylated cytosines, in one or more nucleotide containing compounds (NCC's). Each NCC preferably includes at least one site suspected of being variant, for example by having a base substitution or methylation. The present invention preferably provides data indicative of not only the presence or absence of the variant but also the location of the variant site along the sequence of the NCC. Thus, the present invention preferably provides a greater amount of information than a method that merely indicates the presence or absence of a mutation without also providing the location of the mutation.

The method preferably includes a polymerase chain reaction (PCR) step 150, in which a region including a site of an NCC suspected of being variant is amplified to provide PCR products. One or more probes are combined with the PCR products and subjected to a melting-annealing cycle 152 to prepare a mixture of complexes. The mixture is subjected to temperature gradient (TG) electrophoresis 154 to cause complexes originating from NCC's having a variant to migrate at a different rate from NCC's not having a variant. The complexes are irradiated 156 to provide a spectroscopic signal, which is converted 158 into data that are indicative of the presence or absence of variants in the amplified regions of the NCC. The data may also be indicative of the genotype of the amplified region of the NCC.

The method is discussed in more detail below.

PCR Amplification 150

The polymerase chain reaction for amplifying an NCC is known in the art. According to the present invention, at least one region of an NCC, such as a single or double stranded DNA molecule, may be amplified to provide a PCR product, which can be used to determine the presence or absence of a variant in the NCC. As defined herein, the term PCR product is synonymous with the term amplicon.

Preferably, each region to be amplified has a known sequence and includes at least one location, e.g., at least one base, suspected of being variant. Some amplified regions may contain one or more variants. Not every amplified region, however, necessarily contains a variant. The PCR products prepared from the amplified regions may be homozygote, or heterozygote, depending upon the presence or absence of variants in the NCC.

In a preferred embodiment, a plurality of regions of one or more NCC's are amplified to provide a plurality of respective PCR products. As understood in the art, PCR amplification of many regions may be performed with a single pair of primers or multiplexed using multiple pairs of primers. The latter method reduces the time, labor and the cost of reagents for the assay. Once prepared, the plurality of PCR products may be subjected to TGCE simultaneously within a single capillary.

To facilitate simultaneous analysis, the PCR amplification preferably generates PCR products having lengths that differ by an amount sufficient to allow even sequentially sized PCR products to be separated by electrophoresis, as discussed below. Preferably, the lengths of respective PCR products differ by between about 2 and about 10 bases, such as between about 2 and about 5 bases. Different lengths of PCR products can be prepared, for example, by designing targeted primer pairs including the regions suspected of having SNPs, mutations, or other variants. As understood in the art, moving any specific pair of primers downstream or upstream of the SNP or mutation-containing region allows the size of the PCR products to be adjusted.

Figure 2:
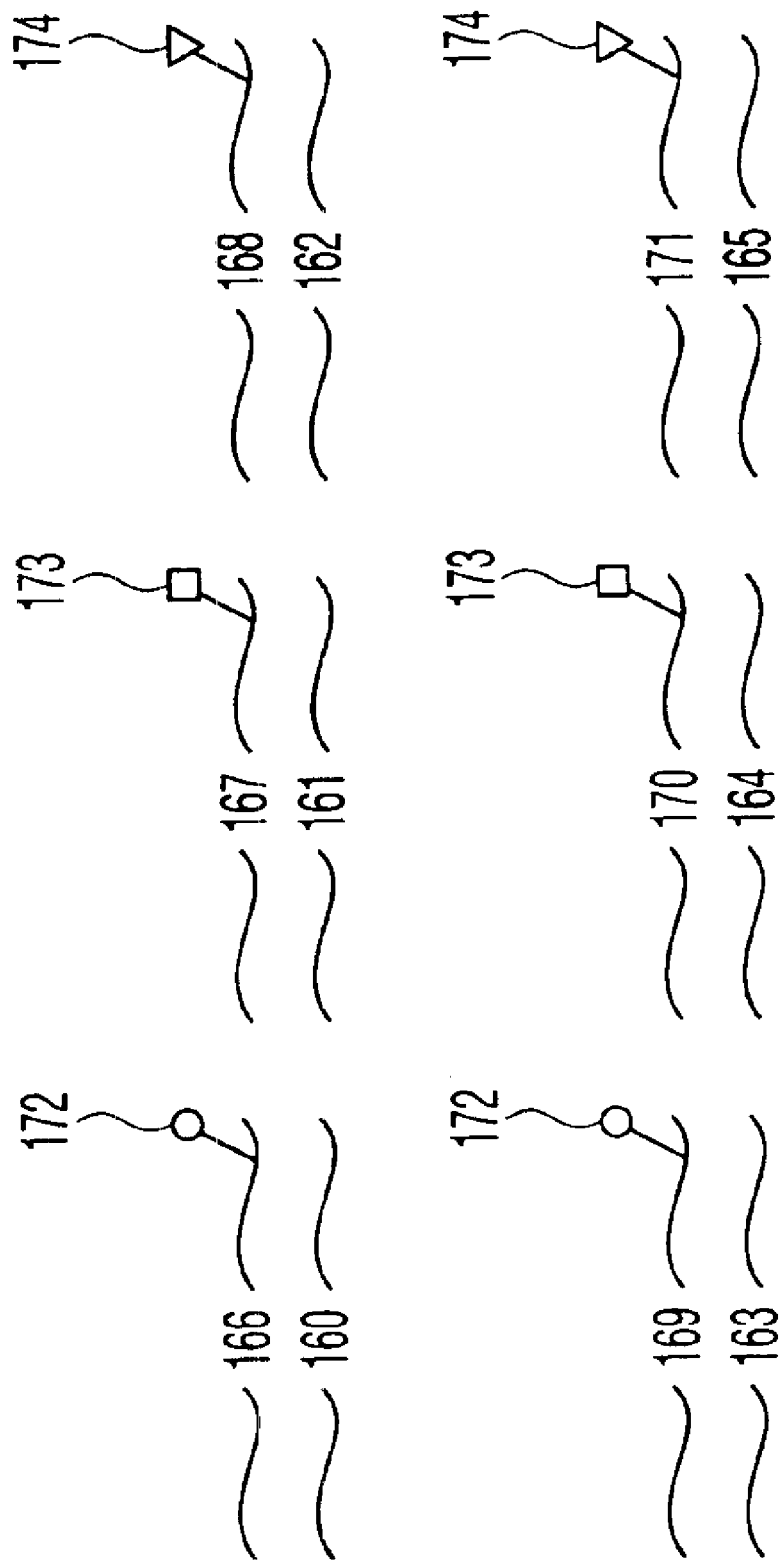
FIG. 2 shows complexes comprising sequentially sized PCR products according to the method of FIG. 1.

Referring to FIG. 2, products 160, 161, 162, 163, 164, and 165 have respective lengths of 100, 105, 110, 115, 120 and 125 bases. A plurality of probes 166, 167, 168, 169, 170, and 171 associate with respective PCR products to form complexes, as discussed below. Complexes containing PCR products 160–165 may be separated using available capillary electrophoresis sieving media and capillaries. The shortest PCR product to be analyzed for the presence of mutations may have a length of less than about 100 bases, such as about 60, 70, or 80 bases. The longest PCR product preferably has a length of less than about 850 base pairs, such as about 800 base pairs or less.

Because complexes comprising respective variant PCR products become separated during electrophoresis, information about the variant status of a given PCR product and, therefore, the NCC from which the PCR product was prepared may be obtained with minimal interference from other PCR products present in the mixture. Thus, up to about 100 different PCR products may be pooled and simultaneously tested for the presence or absence of variants. The products may be pooled and tested for variants without any further post-PCR purification.

It should be understood, however, that PCR amplification is not a required step of the present invention. Rather, PCR amplification is performed, as part of a preferred embodiment, to amplify an amount of NCC suspected of having a variant site. Where an NCC is initially present in an amount sufficient to allow the presence of a variant site to be determined, an amplification step, such as PCR is not required. Rather, the NCC may be tested for the presence of variants by proceeding directly to melting-annealing cycle 152, wherein complexes are formed between one or more probes and the NCC rather than a PCR product. Thus, an NCC not directly prepared from an amplification step may be substituted for a PCR product at any of steps 152, 154, 156, and 158 of FIG. 1.

PNA Probes

One or more PCR products are combined with one or more probes to provide a mixture. Each probe is a molecule that is complementary to at least a portion of a respective one of the PCR products. A probe and a PCR product to which the probe is at least partially complementary will bind to form a complex. A duplex is an example of a complex formed between a PCR product and probe. For example, a probe and its complementary PCR product form a homo-duplex complex. A probe and a PCR product that are partially complementary but have at least one base pair mismatch form a heteroduplex complex. As discussed below, the presence or absence of a mismatch and, therefore, the presence or absence of a variant in the NCC, is determined from TG electrophoresis.

A preferred probe is a peptide nucleic acid (PNA) probe. As defined herein, a PNA is a synthetic nucleic acid in which at least a portion of the sugar-phosphate backbone of DNA is replaced by a preferably uncharged peptide, such as glycine. For example, a PNA probe suitable for use in the present invention includes a DNA analog in which at least a portion of the phosphodiester backbone is replaced by a peptide-containing linkage, such as a 2-aminoethyl-glycine linkage. A preferred PNA probe includes fewer than about 25 nucleotide bases, such as fewer than about 20 nucleotide bases, such as fewer than about 15 nucleotide bases.

PNA probes retain the capability to bind with natural DNA having a complementary base pair sequence. A PNA-DNA complex, however, has a greater thermal stability and higher melting temperature than the corresponding DNA-DNA complex. It should be understood, however, that the present invention is not limited to PNA probes. An example of an alternative probe is an oligonucleotide in which the sugar phosphate backbone has not been replaced with a peptide.

A probe, such as a PNA probe or oligonucleotide probe, may be synthesized to be fully complementary to either the mutation or the wild type DNA sequence. For example, if a particular region of an NCC (and of course of PCR products amplified therefrom) is suspected of having a mutation at its 3' end, the probe may be synthesized to be complementary to the variant form of that region. In this case, the probe will be fully complementary to the mutation type PCR product and will have a mismatch with the wild type PCR product. Alternatively, the probe may be synthesized to be complementary to the wild-type form of the region of interest. In this case, the probe will be complementary to the wild type PCR product and will have a mismatch with the variant type PCR product.

When designing probes to determine the presence of variants in a number of PCR products, the melting temperatures of the complexes may be adjusted to fall within a single temperature gradient by adjusting the probe size and the position of the suspected variant site along the probe. Thus, probes are not limited to determining the presence of a variant at the 3' end of a sequence of NCC or PCR product. Rather, a probe may be designed to determine the presence of a variant at any base within a given region of the NCC or PCR product. For example, a probe may be constructed so that a possibly variant site is aligned with the 3' end, the 5' end, or in the middle of the probe when the probe and PCR product associate to form a complex.

Referring back to FIG. 2, probes constructed to bind with sequentially sized PCR products are preferably tagged with spectroscopically distinguishable fluorescent dyes to reduce genotype scoring errors. For example, probes 166, 167, 168, 169, 170, and 171 bind with PCR products 160–165 respectively. Probes 166 and 169 are tagged with a dye 172 emitting at a first wavelength range. Probes 167 and 170 are tagged with a dye 173 emitting at a second wavelength range. Probes 168 and 171 are tagged with a dye 174 emitting at a third wavelength range. Probes emitting within each range are distinguishable from probes emitting within other ranges.

During electrophoresis, complexes comprising sequentially sized PCR products migrate to the detection region in sequence, with the shorter sequence being detected first. In some situations, however, complexes comprising sequentially sized PCR products will be spatially overlapped. Tagging the probes of complexes that are expected to be detected in sequence with spectroscopically distinguishable tags allows the presence of variants to be determined even if the complexes are overlapped when detected. Preferably, PCR products associated with complexes having spectroscopically indistinguishable tags will be different in length by at least about 15 bases to increase the probability that such complexes will be spatially separated during electrophoresis.

A dye having a fifth wavelength range can be used as an internal molecular standard to calibrate for the migration changes of various complexes in different capillaries. Application of four dyes, together with the calibration with an internal standard improves the accuracy of variant detection.

Melting-Annealing 152

NCC's, such as PCR products, and one or more probes are subjected to melting annealing step 152 to form complexes. An exemplary temperature profile for melting and annealing runs as follows: 1) hold about 3 min at about 95° C., 2) decrease from about 95° C. to about 80° C. at about 3° C./min, 3) decrease from about 80° C. to about 55° C. at about 1° C./min, 4) hold about 20 min at about 55° C., 5) decrease from about 55° C. to about 45° C. at about 1 C./min, 6) decrease from about 45° C. to about 25° C. at about 2° C./min. Alternative temperature profiles may be used as understood in the art.

When one or more PCR products and PNA probes are heated and gradually annealed, homoduplex complexes and/or heteroduplex complexes form between the PCR products and probes. A homoduplex complex is formed when a PNA probe binds to a PCR product having a base sequence that corresponds to the base sequence of the PNA probe. A heteroduplex complex is formed when a PNA probe binds to a PCR product having a base sequence that differs from the base sequence of the PNA probe by at least 1 base. Thus, a heteroduplex complex will include at least one base pair mismatch. Homoduplexes and/or heteroduplexes may also form between corresponding PCR products present in the mixture. However, upon TGCE and irradiation, only PNA-NCC complexes will be detected because only the PNA tag is detected by fluorescence.

Referring to FIGS. 3a–3c, a PNA probe 182 and a double stranded NCC 184 may be subjected to melting and annealing to prepare a mixture 189. PNA probe 182 includes a fluorescent tag 186. The NCC 184 is a wild type genotype (A/A) and includes first and second NCC strands 192 and 193. PNA probe 182 fully matches the genotype of NCC 184. Upon melting annealing 152, PNA probe 182 forms a homoduplex 190 with complementary NCC strand 192. As discussed above, double stranded NCC 184 may be, but is not required to be, a PCR product.

A probe (not shown) can also be prepared to form a homoduplex with NCC strand 193. Thus, probes can be prepared to match the sense or anti-sense of a NCC sequence. Such freedom in probe preparation may be helpful if difficulties are encountered in constructing a particular probe. For example, a particular application may require that a probe have a purine content below some maximum value. In some circumstances, a probe prepared to match the sense of a NCC sequence will exceed the maximum value whereas a probe designed to match the anti-sense will fall below the maximum value.

Figure 4C:
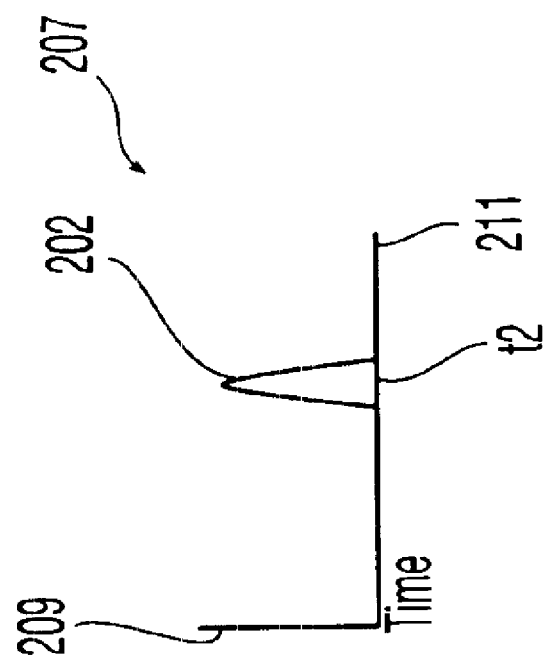
FIG. 4c shows an electropherogram obtained upon temperature gradient electrophoresis and irradiation of the mixture of FIG. 4b.
Figure 4B:
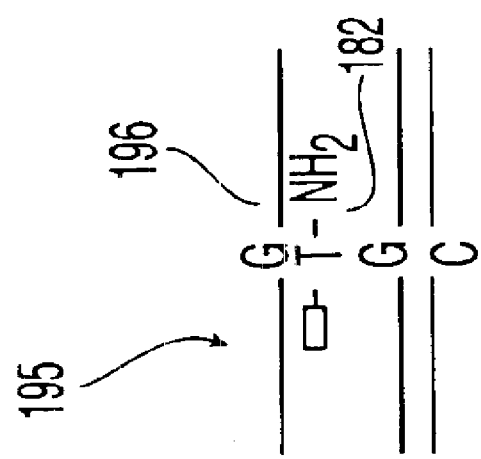
Figure 4A:
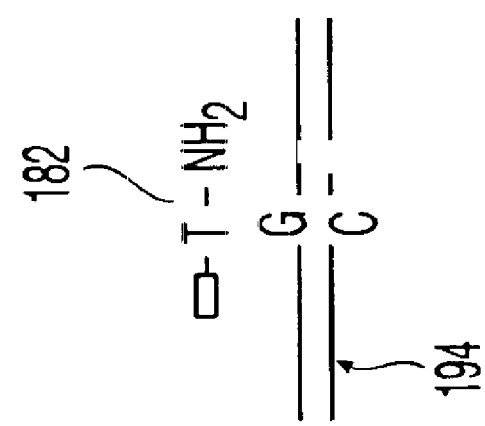
FIG. 4a shows a probe and a nucleotide containing compound according to the method of FIG. 1.

Referring to FIGS. 4a–4c, a PNA probe 182 and a double stranded NCC 194 may be subjected to melting annealing to prepare a mixture 195. The NCC 194 is mutation homozygote (G/G). Upon melting and annealing, PNA probe 182 forms a heteroduplex 196 with the mutation homozygote (G/G). The heteroduplex 196 includes a mismatch, which reduces the melting temperature compared to the homoduplex 190.

Referring to FIGS. 5a–5c, melting and annealing PNA probe 182, NCC 184 and NCC 194 prepares a mixture 198 comprising both homoduplex 190 and heteroduplex 196.

TGCE Separation

The melting point of a complex of a probe and PCR product depends at least in part on the presence or absence of a base pair mismatch in the complex, the length of the probe, and the position along the complex of a mismatch if present. The thermal stability of the complex and, therefore, the melting temperature, depends at least in part on the degree of complementarity between the probe and PCR product. For example, a mismatch at even one base of a probe-PCR product complex is sufficient to reduce the melting temperature of the complex compared to the fully matched complex.

The annealed mixture is subjected to the temperature gradient electrophoresis, such as by temperature gradient capillary electrophoresis (TGCE). During TGCE, the temperature is preferably increased from a temperature below the melting point of all PNA probe-PCR product complexes present in the mixture to a temperature greater than the melting point of all PNA probe-PCR product complexes present. As the temperature is increased, heteroduplex complexes melt prior to corresponding homoduplex complexes because the base pair mismatch reduces the strength of binding between the PNA probe and PCR product of the heteroduplex complex. As a heteroduplex complex begins to melt, its electrophoretic mobility is retarded thereby causing the heteroduplex complex to separate from a corresponding homoduplex complex.

The PNA probes are preferably subjected to irradiation to generate a signal such as laser-induced fluorescence. Only the PNA/DNA duplexes are recorded since only the PNA probes are labeled. The spectroscopic signal is converted to data indicative of the presence or absence of variants in the amplified regions.

Figure 6:
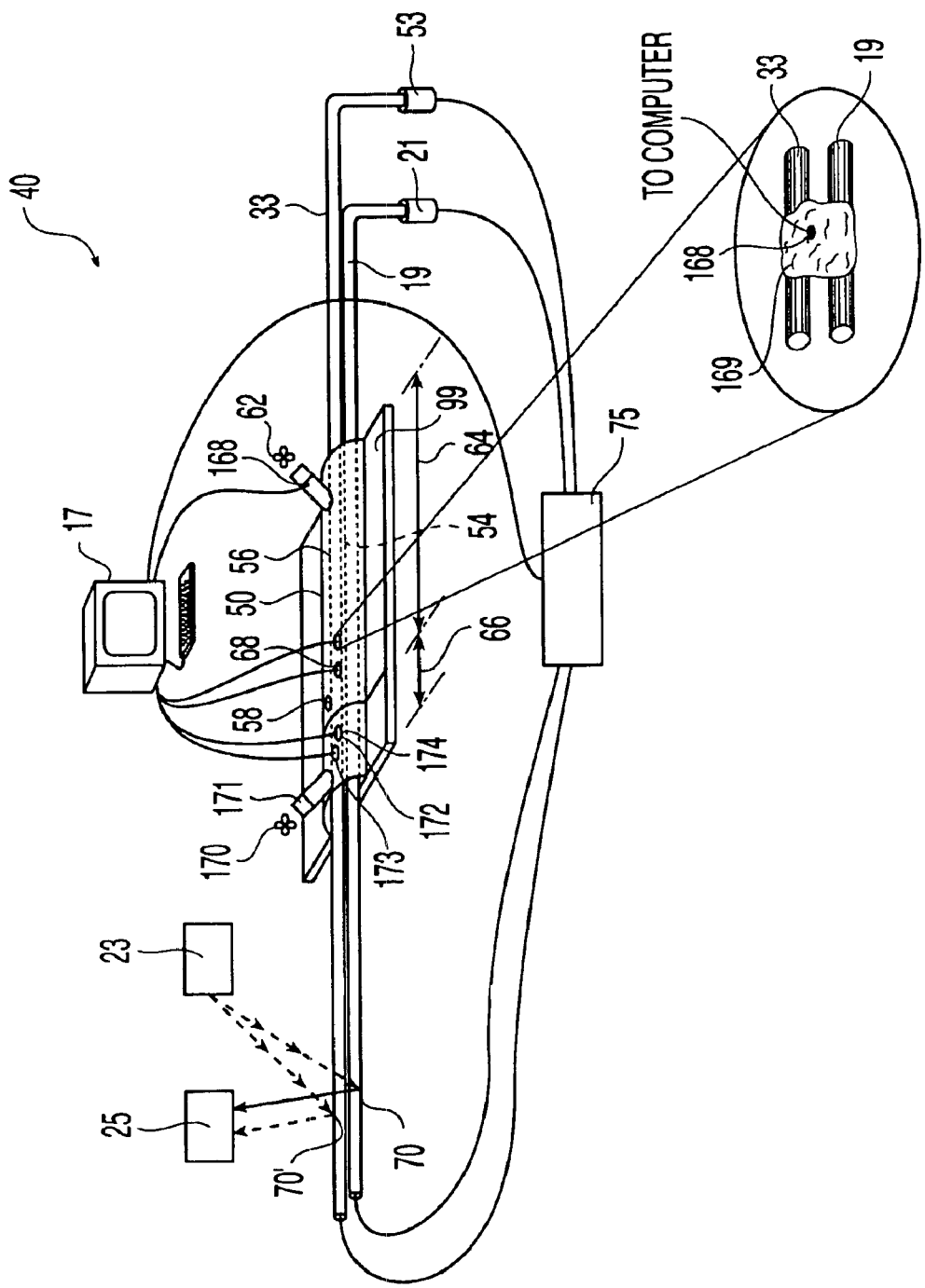
FIG. 6 shows a mutation detection device suitable for use in the method of FIG. 1.

Referring to FIG. 6, a preferred arrangement of an embodiment of a mutation detection device 40 is shown. A sample capillary 33 is provided to electrophoretically separate unknown sample compounds. By capillary it is meant any structure configured and arranged to separate a sample using electrophoresis. Preferred structures include capillaries, microfabricated channels, and planar structures, such as lanes of slab gels. Capillary 33 is arranged to be in fluid contact with a sample reservoir 53, which is configured to contain a volume of sample sufficient to perform an analysis. Examples of suitable sample reservoirs include the wells of a microtitre plate, a structure configured to perform PCR amplification on a volume of sample, a reservoir of a microfabricated lab on a chip device, and the like.

Device 40 is provided with a power supply 75 suitable for providing a sufficient voltage and current for electrophoretic separation of a sample. The power supply is preferably configured to allow at least one of the current or resistance of the capillary to be monitored during a separation. Preferably, the current or resistance data is received by the computing device 17 to allow the electric potential to be varied to maintain a constant current or resistance. This is discussed in more detail below.

A temperature controlled portion 54 of sample capillary 33 is arranged to be in thermal contact with a heat source such as a hot plate 99, or the like. Temperature controlled portion 54 has a length 64. Optionally, or in addition, the external heat source may comprise a wire, filament, or other ohmic heating element arranged external to the capillary. A temperature sensitive device such as a thermocouple 168 is disposed in thermal contact with capillary 33 and reference capillary 19 to determine the temperature of migrating species therein. Thermocouple 168 is in communication with computing device 17, which can adjust the temperature of hotplate 99 to maintain or establish a predetermined temperature or temperature profile.

Alternatively or in combination with hotplate 99, mutation detection system 40 may include an element 62 to cause temperature controlled gas or liquid to flow in thermal contact with capillary 33. The gas or liquid enters at an input port 268 and exits at an exit port 58. The capillary is preferably surrounded by a thermally conductive medium, such as a thermally conductive paste 169, to enhance thermal contact between the heating element and the capillary. Capillary 33 may have a cooled portion 172 having a length 66 to reduce the temperature of migrating compounds prior to detection. An element 170 may be provided to introduce chilled gas or liquid to cooled portion 172 through an entry port 171.

Mutation detection device 40 is preferably provided with an optional reference capillary 19 configured to simultaneously separate a reference sample comprising reference nucleotides. Reference capillary 19 includes a reference reservoir 21 configured to contain the reference sample. Sample and reference capillaries 33 and 19 include respective detection zones 70' and 70.

Device 40 also includes a light source 23, such as a laser emitting a wavelength suitable to generate a spectroscopic signal, such as fluorescence or absorbance from the PNA probe or NCC, such as a PCR product. A detector 25 is arranged to detect the spectroscopic signal, which is converted to data representative of the spectroscopic signal. The data are sent to computing device 17. The spectroscopic signal can be represented by, for example, a time-spectroscopic intensity plot including peaks indicative of the presence of the NCC or probe. A specific example is an electropherogram including a time-fluorescence intensity plot. Another example is an electropherogram including a time-absorbance intensity plot where the absorbance relates to an attenuation of light by the PNA probe and/or NCC. For a time-absorbance measurement, a detector is disposed to measure the intensity of light that has passed generally radially through the separation lane.

In one embodiment, the spectroscopic signal is preferably essentially free of fluorescence resulting from an intercalating dye. This embodiment may be considered an intercalating dye-free method. By essentially free, it is meant that the spectroscopic signal includes an amount of intercalating dye fluorescence that is insufficient to substantially reduce precision of the measurement of the fluorescence from the PNA probe tag. For example, it is preferred that fluorescence from the PNA probe tag be at least 5 times, such as at least 10 times, or at least 30 times greater than fluorescence from an intercalating dye, if such a dye is present. Preferably, essentially no intercalating dye is associated with the PNA probe when the PNA probe is irradiated.

Sieving Media

The TG electrophoresis is preferably conducted by using an electrophoresis medium, such as a sieving medium, that separates migrating species on the basis of size and/or shape. An example of a suitable sieving medium is an electrophoresis gel. The electrophoresis is preferably carried out within the bore of a capillary. Within the bore, the PNA probe and NCC migrate substantially along a migration axis under the influence of an electric field.

A preferred separation medium for mutation detection comprises a buffer, such as 1× TBE buffer, which can be prepared, for example, by dissolving 8.5 g premixed TBE buffer powder (Amerosco, Solon, Ohio) into 500 ml dionized water.

An electrophoresis medium, such as a sieving matrix, can be prepared using Polyvinylpyrrolidone (PVP) which is available from Sigma (St. Louis, Mo.). A preferred sieving matrix can be made by dissolving about 0.5% to about 6% (w/v) of 360,000 M PVP into 1× TBE buffer. Preferably, the amount of PVP is about 3% (w/v). The viscosity of a three percent solution is less than 10 cp. The use of polyvinylpyrrolidone makes the capillary regeneration process very easy to implement. The capillaries have a negligible failure rate even over several months. The excellent EOF suppressing effect of the PVP medium enhances the reproducibility of and decreases uncertainty associated with mutation detection. Alternatively the separation medium includes other sieving matrices such as polyacrylamide gels.

Preferably, substantially all of the PNA present in the electrophoresis medium is free to migrate under the influence of an electric field. Thus, the electrophoresis medium is preferably essentially free of entrapped PNA. More preferably, the electrophoresis medium is completely free of entrapped peptide nucleic acid. By essentially free, it is meant that the electrophoresis medium entraps an amount, if any, of PNA that is insufficient to retard the migration of a nucleotide containing compound complementary to the PNA. If however, any PNA is entrapped by the electrophoresis medium, it is preferred that the entrapped PNA be substantially non-binding with an NCC whose mutation status is to be determined by the temperature gradient electrophoresis. By substantially non-binding, it is meant that the temperature of the sieving medium is greater than the melting temperature of the migrating NCC and the entrapped PNA probe, if present.

TGCE Temperature Profiles

A temperature profile of the invention preferably includes at least one change in the temperature of the separation medium as a function of time. Temperatures during a temperature profile can be varied over any time and temperature range sufficient to induce a mobility differential between samples to be separated. Preferred temperature extremes include a minimum of at least about 0° C. and a maximum of about 100° C. Preferably, the temperature within the temperature control zone is substantially constant along a dimension of the separation medium that is perpendicular to the direction of migration. By substantially constant temperature it is meant that the spatial temperature variations are insufficient to introduce measurable mobility variations for compounds disposed at different spatial locations within the temperature control zone at any given instant. Thus, at any given instant, the temperature at any point along the portion of each capillary within the temperature control zone is preferably constant, i.e., there are substantially no spatial temperature gradients in the temperature control zone.

The application of a temperature sufficient to overcome at least some interaction forces holding together a complex comprising a PNA probe and a nucleotide containing compound, will at least partially denature the PNA probe-NCC complex. A complex containing a base pair mismatch between the PNA probe and NCC (defined herein as a heteroduplex complex) will melt (denature) at a lower temperature than a complex having no base pair mismatch between the PNA probe and NCC (defined herein as a homoduplex complex). Therefore, in an electrophoresis medium, such as a gel or a long chain linear polymer solution, the heteroduplex and homoduplex complexes can be separated or otherwise distinguished by providing, for at least a portion of the electrophoresis, a temperature sufficient to melt the heteroduplex complex but not the homoduplex complex.

Increasing the temperature of the separation medium from an initial value that is less than the melting temperature of both the homoduplex complex and the heteroduplex complex, will cause the heteroduplex complex to exhibit a retarded migration behavior near its melting temperature compared to the homoduplex complex. As the temperature is raised above the melting temperature of the homoduplex complex, the difference in mobilities between the pair of compounds is reduced. Thus, separation between a homoduplex complex and heteroduplex complex depends in part on the total amount of time the separation medium is at a temperature above the melting point of the heteroduplex complex but less than the melting temperature of the homoduplex complex. The mutation can be identified by the difference in the resulting electrophoretic patterns between the homoduplex complex and the heteroduplex complex.

For accurate comparison of the patterns, a reproducible temperature profile is required. Because in this invention the temperature of the separation medium can be varied independently of the electric field, arbitrary temperature variation profiles can be selected. For the separation of heteroduplex complexes using an apparatus and temperature profile of the present invention, migration times have a relative standard deviation of less than 2%.

Since the mobility retardation (differential mobilities between a heteroduplex and corresponding homoduplex complex) occurs only when the complexes begin to melt, the part of the capillary that is not elevated above the melting temperature of a fragment, will not affect the differential mobility of the fragments. Preferably, a temperature profile of the invention is not begun until at least some and preferably substantially all components in a sample have migrated into the temperature control zone.

Detection of Variants

As discussed above with reference to FIGS. 3–5, a mixture of a probe and an NCC, such as a PCR product, representing a unique locus can be either heterozygous (containing both alleles) or homozygous (containing one or the other allele). TGCE of the mixture is generally sufficient to determine whether the mixture is homozygous or heterozygous. In particular, different spectroscopic signals will be obtained upon irradiation of mixtures containing one or the other allele or a combination of alleles. When the spectroscopic signals are converted to, for example, electropherograms, the differences will appear in the number of peaks present and migration time of the peaks.

Referring to FIG. 3c, spectroscopic signals from TGCE of melted-annealed mixture 189 are represented as an electropherogram 201 having a spectroscopic intensity axis 203 and a time axis 205. Homoduplex 190 formed of homozygous NCC 184 fully matched to PNA probe 182 produces a single peak 200 upon irradiation. Peak 200 has a migration time $t_1$ along time axis 205.

Referring to FIG. 4c, data from TGCE of melted-annealed mixture 195 is represented as an electropherogram 207 having a spectroscopic intensity axis 209 and a time axis 211. Heteroduplex 196 formed of homozygous mutation NCC 194 having a mismatch with PNA probe 182 produces a single peak 202 upon irradiation. Peak 202, indicative of the presence of the heteroduplex, has a migration time of time $t_2$ along time axis 211.

Time $t_2$ is greater than time $t_1$ because the mismatch present in heteroduplex 196 reduces its melting temperature relative to homoduplex 190. Therefore, as the temperature is raised during temperature gradient electrophoresis, heteroduplex 196 melts prior to homoduplex 190. As a complex melts, its migration is retarded. Thus, the earlier melting complex, which includes a mismatch, will have the longer migration time.

Referring to FIG. 5c, two peaks result when annealed mixture 198, which contains both heteroduplex 196 and homoduplex 190, is subjected to TGCE and irradiation to obtain a spectroscopic signal. The spectroscopic signal is shown as an electropherogram 213 having a time axis 214 and a spectroscopic intensity axis 216. Electropherogram 213 contains a first faster moving peak 215 and a second, slower moving peak 217. Faster peak 215 corresponds to the presence of the homoduplex 190 and slower peak 217 corresponds to the presence of the heteroduplex 196. The presence of two peaks is indicative of a heterozygous mixture.

In some cases, the migration time difference between a homoduplex and a heteroduplex will be insufficiently large to determine the presence or absence of the mismatched peaks. Small migration time differences are particularly problematic when the different mixtures are subjected to TGCE in different capillaries because capillary-to-capillary performance variations may obscure the small migration time differences. According to the invention, two or more spectroscopically distinguishable probes may be used to genotype a mixture even where migration time variations are small.

Figure 7C:
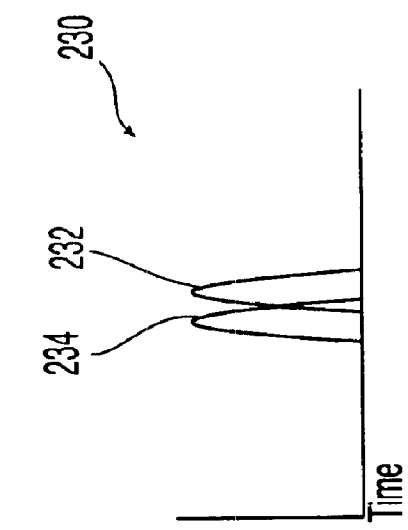
FIG. 7c shows an electropherogram obtained upon temperature gradient electrophoresis and irradiation of the mixture of FIG. 7b.
Figure 7B:
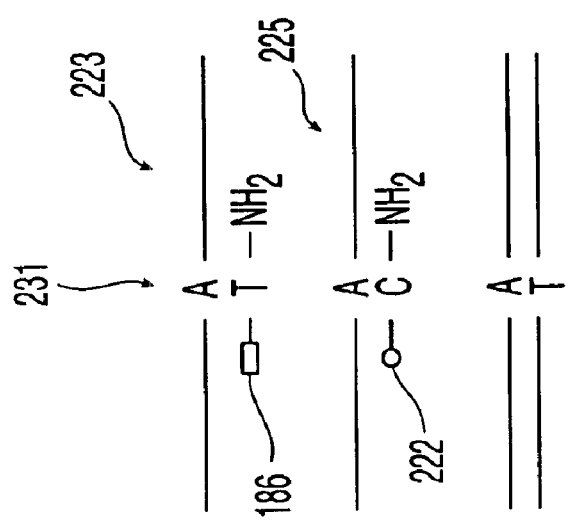
Figure 7A:
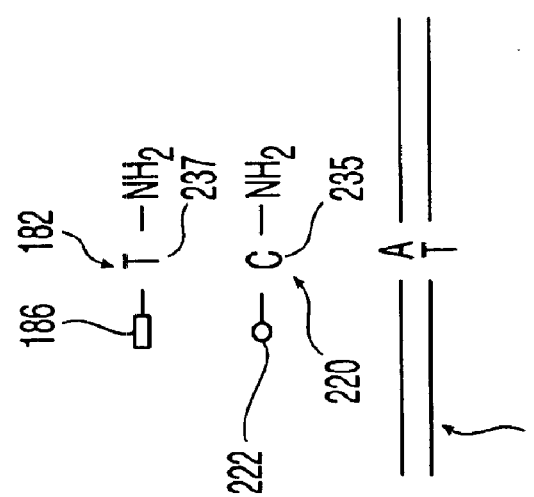
FIG. 7a shows probes and a nucleotide containing compound according to the method of FIG. 1.
Figure 8C:
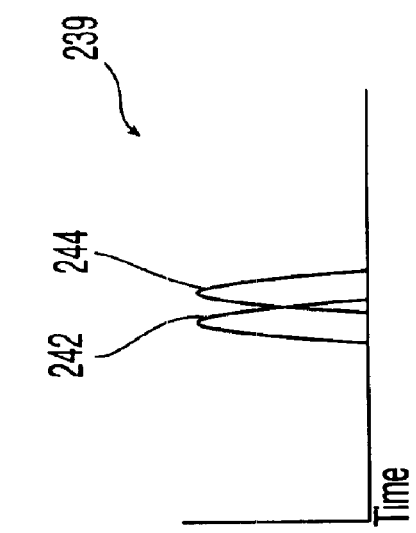
FIG. 8c shows an electropherogram obtained upon temperature gradient electrophoresis and irradiation of the mixture of FIG. 8b.
Figure 8B:
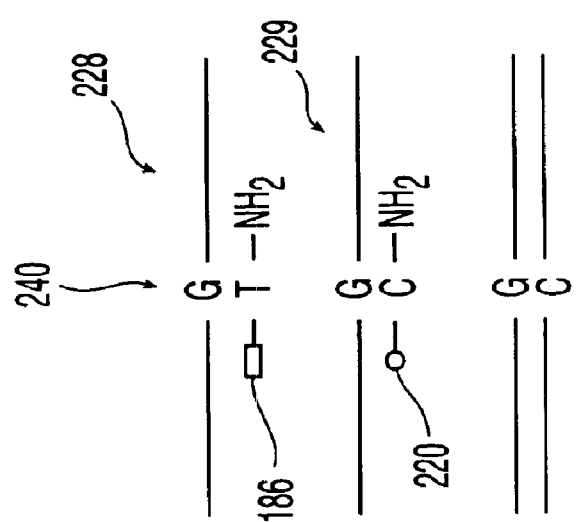
Figure 8A:
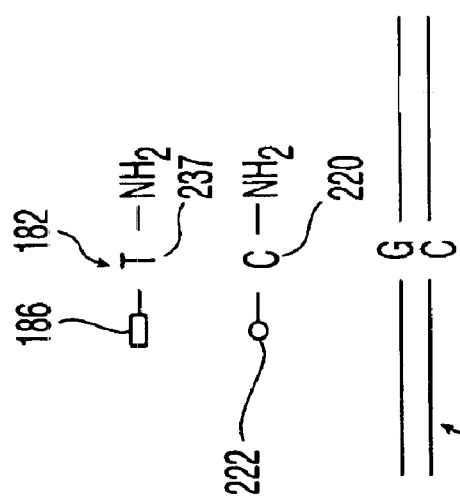
FIG. 8a shows probes and a nucleotide containing compound according to the method of FIG. 1.

Referring to FIGS. 7 and 8, PNA probe 182 is designed to fully match NCC 184 (the wild type genotype (A/A), while a probe 220 matches to NCC 194 (mutation homozygote (G/G). Probe 220 includes a fluorescent tag 222, which can be distinguished spectroscopically from fluorescent tag 186. Probe 220 is identical to probe 182 except for the different tag and the substitution of a cytosine 235 in place of a thymine 237. Preferably, fluorescent tag 222 emits at least one different wavelength from tag 186. The tags may also be distinguishable on the basis of emission lifetime.

Upon combining both probes 182 and 220 with either NCC 184 or NCC 194, both a PNA-NCC homoduplex and a PNA-NCC heteroduplex are formed. For example, melting annealing NCC 184 and probes 182 and 220 prepares a mixture 231 comprising a homoduplex 223 and a heteroduplex 225. Melting annealing NCC 194 and probes 182 and 220 prepares a mixture 240 comprising a homoduplex 229 and a heteroduplex 228.

During TGCE, each fully matched homoduplex 223 and 229 has a shorter migration time than the mismatched heteroduplex 225 and 228. An electropherogram 230 is obtained when melted annealed mixture 231 is subjected to TGCE. Electropherogram 230 includes a peak 232 associated with fluorescence of tag 222 and a peak 234 associated with fluorescence of tag 186. An electropherogram 239 is obtained when melted annealed mixture 240 is subjected to TGCE. Electropherogram 239 includes a peak 242 associated with fluorescence of tag 222 and a peak 244 associated with fluorescence of tag 186.

The genotype of the sample can be determined from the spectroscopic signal. For example, the wavelength of the fluorescence associated with the slower migrating heteroduplex will be different depending upon the genotype. For an NCC with base pair A/T, fluorescence associated with tag 222 will be slower moving whereas for an NCC with base pair G/C, fluorescence associated with tag 186 will be slower moving. The difference in migration time for fully matched and mismatched PNA-DNA duplexes can be tested in pilot study before launching a large-scale genotyping.

Multiplexed Variant Detection

The present method allows simultaneous screening of up to thousands of PCR products with different melting temperatures in a single run using instruments having more than one electrophoresis capillaries. An automated parallel capillary electrophoresis system having a plurality of capillaries, such as that described in U.S. Pat. No. 6,027,627, can be used. In this case, a heating element imposes an identical temperature gradient on all 96 capillaries. Because of the low heat capacity of each capillary, the results will be similar to those for a single capillary. The present invention is suitable for use with a two-dimensional array of capillaries having a spacing corresponding to that of an array of sample containers, such as the wells of a microtitre tray, to simultaneously introduce a plurality of samples, such as the products of PCR amplification.

One out of 96 capillaries preferably serves as a control capillary for all samples to be tested in the remaining 95 capillaries. The control run, as all sample runs, should include all multiplexed PCR products and probes. An internal molecular ladder with fluorescence different from tagged PNA dyes will be utilized to estimate the locations of each PNA-DNA complex (and thus the sample identity) and calibrate for the migration changes of various duplexes in different capillaries. The genotype for each PCR product will be scored based on the length of the PCR product, the fluorescence of the PNA probe and difference in migration time between the homoduplex and the heteroduplex.

The present invention allows the presence or absence of variants to be simultaneously determined in a plurality of DNA fragments. For example, a standard sequencing capillary can separate DNA fragments having lengths of up to about 800 base pairs. Thus, for example, about 100 DNA fragments having lengths of 5–7 bp apart can be analyzed in a single capillary. Using different fluorescently tagged PNA probes can further increase the number of testing samples separated in a capillary. The identity of each genotype can be determined by the fragment size and corresponding fluorescence. Thus, the method will allow simultaneous screening of thousands of samples with different melting temperatures in a single run with a fully automated 96-capillary instrument.

Determination of Methylated Cytosines

The present invention may be used for obtaining data indicative of the presence of variants comprising one or more methylated cytosines in a nucleotide-containing compound (NCC), such as a DNA sequence. Preferably the data are indicative of whether a particular cytosine of the NCC is methylated. By particular cytosine, it is meant a cytosine having a known location along the sequence of the NCC. Thus, the present invention preferably provides a greater amount of information than a method that merely indicates that a particular NCC lacks or includes a methylated cytosine without providing the position of the methylated cytosine.

The NCC is preferably contacted with a compound composed to replace non-methylated cytosines of the NCC with another base to provide a modified NCC. The modified NCC is subjected to temperature gradient electrophoresis in the presence of one or more PNA probes, whereby spectroscopic signals are obtained. The spectroscopic signals are converted to the data indicative of the presence and, preferably, location of the one or more methylated cytosines. The modified NCC may be subjected to amplification, such as by PCR, prior to temperature gradient electrophoresis.

Sample Modification

Figure 9:
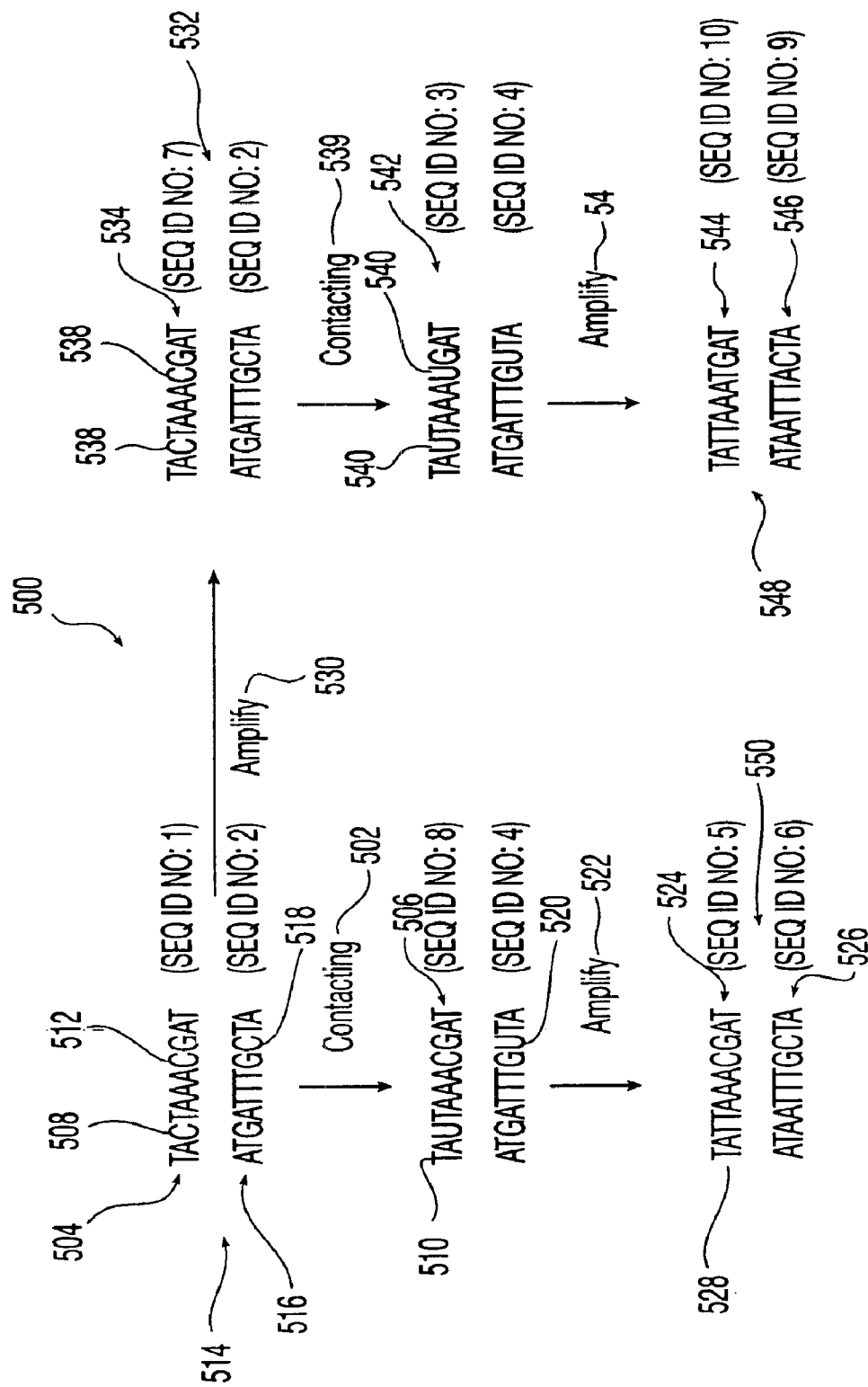
FIG. 9 shows a flow chart of shows steps of a method for determining the presence of methylated cytosines (SEQ ID NO: 1 through SEQ ID NO:9) according to the invention.

Referring to a flow chart 500 of FIG. 9, a method for methylated cytosine determination includes a contacting step 502, which includes contacting an NCC 504 with a compound suitable to provide a modified NCC 506 in which non-methylated cytosines 508 have been replaced with a different base. An NCC to be tested for the presence of methylated cytosines may comprise only a single sequence of nucleotides or can comprise a plurality of sequences of nucleotides. For example, NCC 514 is but one strand of a double stranded NCC 514 that also includes a single strand NCC 516, which is complementary to NCC 514. It is preferred that the doubled stranded NCC be denatured during the contacting step.

A preferred compound for use in the contacting step is a bisulfite salt, such as sodium bisulfite $NaHSO_3$, which replaces non-methylated cytosines of an NCC with uracil 510. U.S. Pat. No. 6,017,704 to Herman et al., which is incorporated herein to the extent necessary to understand the present invention, discloses suitable methylation specific bisulfite chemistry that replaces non-methylated cytosines with uracil. It should be understood, however, that compounds other than bisulfite that similarly modify non-methylated cytosine, but not methylated cytosine can also be used in the method of the invention.

Sodium bisulfite reacts readily with the 5,6-double bond of cytosine, but poorly with methylated cytosine. Cytosine reacts with the bisulfite ion to form a sulfonated cytosine reaction intermediate, which is susceptible to deamination, giving rise to a sulfonated uracil. The sulfonate group can be removed under alkaline conditions, resulting in the formation of uracil. Uracil is recognized as a thymine by Taq polymerase and therefore, upon PCR, the resultant product contains cytosine only at the position where methylated cytosines occur. Thus, following the contacting step, the only remaining cytosines of the NCC are methylated. Non-methylated cytosines 518 of NCC 516 are preferably replaced with the same base that replaced non-methylated cytosines of NCC 504.

Once non-methylated cytosines of NCC 504 have been replaced with another base, at least a portion of modified NCC 506 is amplified 522 via a polymerase chain reaction (PCR). The amplification is preferably performed in the presence of strand-specific primers, which amplify only modified NCC 506 to provide a PCR product NCC 524. The primers comprise two or more deoxyribonucleotides or ribonucleotides, preferably more than three, and most preferably more than 8, which sequence is capable of initiating synthesis of a complementary primer extension product.

The amplification is preferably performed in the presence of nucleoside triphosphates, an agent for polymerization, such as DNA polymerase, and a suitable temperature and pH.

If the NCC is one strand of a double-stranded NCC, the strand-specific primers amplify only the NCC that is to be analyzed to determine the presence of methylated cytosines. Thus, for example, complementary sequence 516 is preferably not amplified. Using strand-specific primers preferably provides PCR products comprising only PCR product 524 and a complementary PCR product sequence 526. In the annealed state, the PCR product 524 and complementary PCR product sequence 526 form a double stranded nucleotide containing compound (DNSCC) 550.

During amplification 522, the bases that had been replaced during the denature/replace step 502 are preferably replaced with another base. For example, uracil bases 510 of modified NCC 506 are preferably converted to another base, such as thymine 528.

Analysis of Modified Samples

To obtain data indicative of the presence of one or more methylated cytosines in NCC 504, PCR products obtained by amplifying modified NCC 506 are combined with one or more probes, and subjected to melting-annealing to prepare a mixture comprising complexes of the PCR products and the probes. A probe to be combined with the PCR products is preferably complementary with at least a portion of the PCR products. The presence or absence of a methylated cytosine at a particular location of the original unmodified NCC determines whether a complex of the PCR product and probe will be a heteroduplex or a homoduplex. Thus, the presence or absence of the methylated cytosine can be determined by determining whether the mixture comprises a heteroduplex or homoduplex, such as by using TGCE.

Figure 10A:
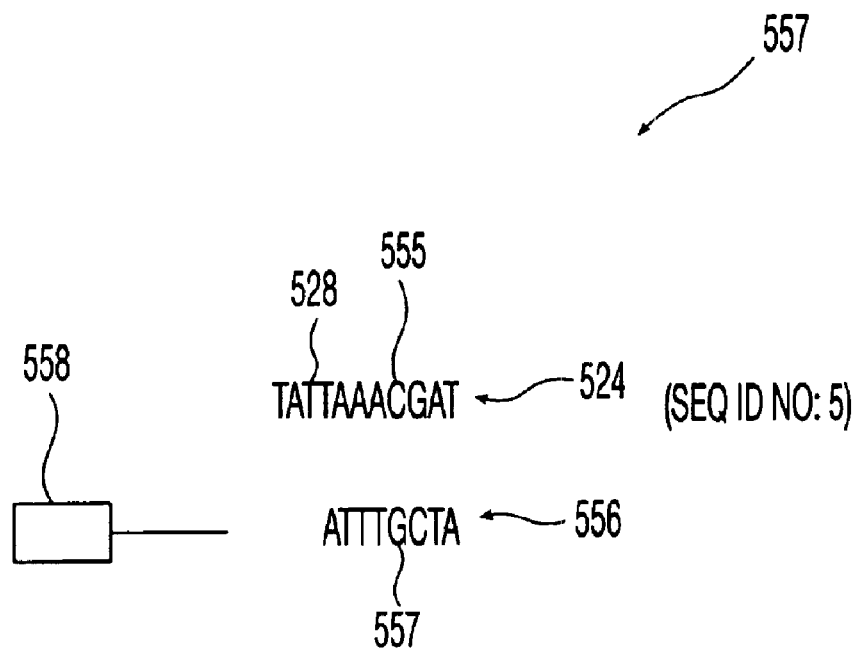
FIGS. 10a and 10b show a probe and PCR products (SEQ ID NO: 10) according to the methods of FIG. 1 and FIG. 9.

Referring to FIG. 10*a*, for example, PCR product 524 includes a cytosine 555 at a site corresponding to methylated cytosine 512 of unmodified NCC 504, which is seen in FIG. 9. A PNA probe 556 is constructed to hybridize to a region of PCR product 524 that includes cytosine 555, i.e., the site corresponding to cytosine 512 of unmodified NCC 504. PNA Probe 562 includes a guanine 557 at the site corresponding to cytosine 512. Thus, PNA probe 556 and PCR product 524 are fully complementary and will form a homoduplex 557 upon melting and annealing. PNA probe 556 also includes a fluorescent tag 558.

Figure 10B:
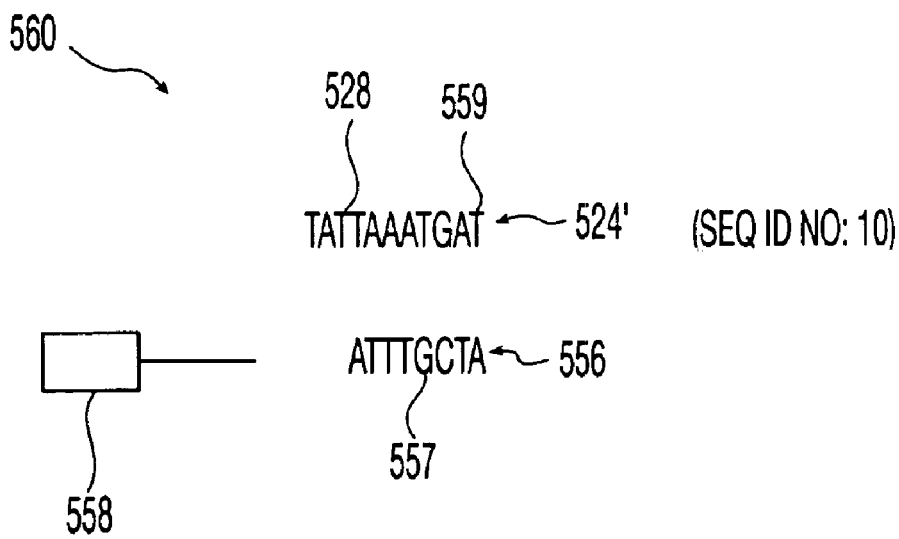

Referring to FIG. 10*b*, a PCR product 524' represents the PCR product that would be obtained from NCC 504 if cytosine 512 had been unmethylated rather than methylated. The only difference between PCR product 524' and PCR product 524 is that PCR product 524' includes a thymine 559 at the site at which PCR product includes cytosine 555. Thus, when PCR product 524' is melted annealed with probe 556, the two combine to form a heteroduplex 560 because the thymine 559 is not complementary to the G 557.

Data converted from a spectroscopic signal obtained upon TGCE and irradiation of a mixture comprising homoduplex 557 will include a peak have shorter migration time than a spectroscopic signal obtained from a mixture comprising heteroduplex 560. If the shorter migration time is observed, the data indicate that the original NCC included a methylated cytosine. Moreover, the data also indicate the location of the methylated cytosine because the probe was constructed to target a particular site of the PCR product. If the longer migration time is observed, the data indicate that the original NCC did not include a methylated cytosine.

Of course, one could design a PNA probe to form a homoduplex with PCR products formed from an unmethylated NCC. In this case, the shorter migration time would correspond to the absence of a methylated cytosine in the unmodified NCC.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A peptide nucleic acid probe-based method for generating data indicative of the presence of a variant in a nucleotide containing compound, comprising:

subjecting a peptide nucleic acid probe (PNAP) having fewer than about 30 bases to temperature gradient electrophoresis in the presence of a nucleotide containing compound (NCC), wherein, during temperature gradient electrophoresis, the PNAP and the NCC are subjected to a first temperature and a second, different temperature and, during at least a portion of the temperature gradient electrophoresis, the PNAP and NCC migrate electrophoretically, wherein:

(a) one of the first and second temperatures is sufficient to retard electrophoretic migration of a first duplex comprising the PNAP and the NCC relative to a second duplex comprising the PNAP and the NCC if the first duplex comprises a mismatch between the PNAIP and NCC and the second duplex lacks the mismatch between the PNAP and NCC; and (b) the other of the first and second temperatures is insufficient to retard an electrophoretic migration of the first duplex relative to the second duplex;

irradiating at least the PNAP to generate a spectroscopic signal; and converting the spectroscopic signal into data suitable for determining the presence of the variant in the NCC.

2. The method of claim 1, wherein the PNAP comprises fewer than about 20 bases.

3. The method of claim 1, wherein, at the beginning of the temperature gradient electrophoresis, the PNAP is bound to the NCC.

4. The method of claim 1, wherein the PNAP comprises a fluorescent tag and the spectroscopic signal results from the fluorescent tag.

5. The method of claim 1, wherein the data suitable for determining the presence of the variant are essentially free of data resulting from intercalating dye fluorescence.

6. The method of claim 1, wherein the temperature gradient electrophoresis is conducted using a sieving medium that is essentially free of entrapped PNAP.

7. A peptide nucleic acid probe-based method for determining the presence of a variant in a nucleotide containing compound, comprising:

providing a first peptide nucleic acid probe (PNAP) and a second PNAP, the first and second PNAP's being spectroscopically distinguishable from one another;

obtaining a first parameter representative of a first spectroscopic signal resulting from the first PNAP, the first PNAP having been subjected to temperature gradient electrophoresis in the presence of the nucleotide containing compound;

obtaining a second parameter representative of a second spectroscopic signal resulting from the second PNAP, the second PNAP having been subjected, simultaneously with the first PNAP, to temperature gradient electrophoresis in the presence of the nucleotide containing compound, wherein, during temperature gradient electrophoresis, the first PNAP and the nucleotide containing compound form a first duplex and the second PNAP and the nucleotide containing compound form a second duplex, the first duplex havina at least one more mismatch than the second duplex, and wherein, during temperature gradient electrophoresis, the first PNAP, the second PNAP, and the nucleotide containing compound are subjected to first and second temperatures, wherein:
  (a) one of the first and second temperatures is sufficient to retard electrophoretic migration of the first duplex relative to the second duplex; and
  (b) the other of the first and second temperatures is insufficient retard electrophoretic migration of the first duplex relative to the second duplex; and
comparing the first and second parameters to determine the presence of the variant in the nucleotide-containing compound.

8. The method of claim 7, wherein the first and second PNAP's each comprise fewer than about 20 bases.

9. The method of claim 7, wherein the each PNAP comprises a respective fluorescent tag and the first and second spectroscopic signals result from the respective fluorescent tags.

10. The method of claim 7, wherein the respective fluorescent tags emit fluorescence at different wavelengths.

11. The method of claim 7, wherein the first and second spectroscopic signals used to obtain the first and second parameters are essentially free of fluorescence resulting from an intercalating dye.

12. A peptide nucleic acid probe-based method for determining the presence of variants in a plurality of respective nucleotide containing compounds, comprising:
  subjecting a mixture comprising a plurality of different peptide nucleic acid probes (PNAP's) and a plurality of different nucleotide containing compounds (NCC's) to temperature gradient electrophoresis, different NCC's having a different length, respective PNAP's forming complexes with respective NCC's of different lengths, wherein, during temperature gradient electrophoresis, for each of at least two of the complexes, the peptide nucleic acid probe (PNAP) of the complex and the nucleotide containing compound (NCC) of the complex are subjected to a respective first temperature and a respective second temperature, wherein, for each of the at least two complexes:
    (a) one of the first and second temperatures is sufficient to retard the electrophoretic migration of a mismatched complex relative to a complementary complex, the mismatched complex comprising at least one mismatch between the PNAP and the NCC, the complementary complex lacking the mismatch; and
    (b) the other of the first and second temperatures is insufficient to retard the electrophoretic migration of the mismatched complex relative to the complementary complex;
  irradiating the peptide nucleic acid probes to generate spectroscopic signals; and
  converting the spectroscopic signals into data suitable for determining the presence of variants in respective nucleotide-containing compounds.

13. The method of claim 12, wherein the different nucleotide containing compounds comprises at least 4 nucleotide containing compounds having lengths that differ by between about 2 and about 10 bases.

14. The method of claim 12, wherein the mixture is subjected to electrophoresis within a single separation lane.

15. The method of claim 12, wherein the mixture includes at least about 10 different peptide nucleic acid probes and at least about 10 different nucleotide containing compounds.

16. The method of claim 15, wherein the mixture includes at least about 25 different peptide nucleic acid probes and at least about 25 different nucleotide containing compounds.

17. The method of claim 12, wherein the peptide nucleic acid probes comprise a respective fluorescent tag.

18. The method of claim 12, wherein the spectroscopic signals are essentially free of fluorescence resulting from an intercalating dye.

19. A temperature gradient electrophoresis-based method for generating data indicative of the presence of one or more methylated cytosines in a sample comprising a first nucleotide containing compound (NCC) having non-methylated cytosines, comprising:
  contacting the first NCC with a first compound to thereby provide a modified NCC wherein non-methylated cytosines of the first NCC are replaced with a different base;
  amplifying the modified NCC to obtain first PCR products;
  combining the first PCR products with a plurality of peptide nucleic acid probes to prepare first and second duplexes, each duplex comprising a first PCR product and a peptide nucleic acid probe, the first duplex comprising at least one mismatch, the second duplex lacking the mismatch;
  subjecting the first and second duplexes to temperature gradient electrophoresis, wherein during the temperature gradient electrophoresis, the first and second duplexes are subjected to first and second temperatures, wherein:
    (a) one of the first and second temperatures is sufficient to retard electrophoretic migration of the first duplex relative to the second duplex; and
    (b) the other of the first and second temperatures is insufficient to retard electrophoretic migration of the first duplex relative to the second duplex;
  irradiating the first PCR products and the peptide nucleic acids with light to thereby generate a spectroscopic signal; and
  converting the spectroscopic signal into data indicative of the presence of the one or more methylated cytosines in the first NCC.

20. A temperature gradient electrophoresis-based method for generating data indicative of the presence of one or more methylated cytosines in a sample comprising a first nucleotide containing compound (NCC), comprising:
  obtaining first PCR products, the PCR products having been prepared by: (a1) contacting the first NCC with a first compound to thereby provide a modified NCC in which non-methylated cytosines are replaced with a different base, and (a2) amplifying the modified NCC to obtain said first PCR products;

combining the first PCR products with a plurality of peptide nucleic acid probes to prepare first and second duplexes, each duplex comprising a first PCR product and a peptide nucleic acid probe, the first duplex comprising at least one mismatch, the second duplex lacking the mismatch;

subjecting the first and second duplexes to temperature gradient electrophoresis, wherein during the temperature gradient electrophoresis, the first and second duplexes are subjected to first and second temperatures, wherein:

(a) one of the first and second temperatures is sufficient to retard electrophoretic migration of the first duplex relative to the second duplex; and (b) the other of the first and second temperatures is insufficient to retard electrophoretic migration of the first duplex relative to the second duplex, irradiating the first PCR products and peptide nucleic acids with light to thereby generate a spectroscopic signal; and converting the spectroscopic signal into data indicative of the presence of the one or more methylated cytosines in the first NCC.

21. A peptide nucleic acid probe-based method for generating data indicative of a sequence of at least a portion of the nucleotide-containing compound, comprising:

providing first and second peptide nucleic acid probes (PNAP's) and a nucleotide containing compound (NCC);

combining the first PNAP, second PNAP, and the NCC to prepare first duplexes comprising the first PNAP and the NCC and second duplexes comprising the second PNAP and the NCC;

subjecting the first and second duplexes to temperature gradient electrophoresis, the first and second PNAP's having spectroscopically distinguishable tags, the first PNAP having a sequence corresponding to a first portion of the NCC, the second PNAP having a sequence corresponding to a second, different portion of the NCC and further wherein, during temperature gradient electrophoresis, each of the first and second duplexes are subjected to a respective first temperature and a respective second temperature, wherein, for each of the first and second duplexes:

(a) one of the first and second temperatures is sufficient to retard the electrophoretic migration of a mismatched complex comprising the respective first or second PNAP and the NCC relative to a complementary complex comprising the respective first or second PNAP and the NCC, the mismatched complex comprising at least one mismatch between the respective first or second PNAP and the NCC, the complementary complex lacking the mismatch; and (b) the other of the first and second temperatures is insufficient to retard the electrophoretic migration of the complementary complex relative to the mismatched complex;

irradiating the first and second PNAP's to generate a spectroscopic signal; and converting the spectroscopic signal into data suitable for determining the sequence of at least a portion of the nucleotide-containing compound.

22. A peptide nucleic acid probe-based method for generating data indicative of the presence of a variant in a nucleotide containing compound (NCC), comprising:

subjecting a peptide nucleic acid probe (PNAP) to temperature gradient electrophoresis in the presence of an NCC, wherein the NCC comprises at least about 10 times as many bases as the PNAP, wherein, during at least a portion of the temperature gradient electrophoresis, the PNAP and NCC migrate electrophoretically and, during temperature gradient electrophoresis, the PNAP and the NCC are subjected to a first temperature and a second, different temperature, wherein:

(a) one of the first and second temperatures is sufficient to retard electrophoretic migration of a first duplex comprising the PNAP and the NCC relative to a second duplex comprising the PNAP and the NCC if the first duplex comprises a mismatch between the PNAP and NCC and the second duplexes lacks the mismatch between the PNAP and NCC; and (b) the other of the first and second temperatures is insufficient to retard an electrophoretic migration of the first duplex relative to the second duplex;

irradiating the PNAP to generate a spectroscopic signal; and converting the spectroscopic signal into data suitable for determining the presence of the variant in the nucleotide-containing compound.

* * * * *